(12) United States Patent
Sabelle et al.

(10) Patent No.: US 7,132,534 B2
(45) Date of Patent: Nov. 7, 2006

(54) PARA-PHENYLENEDIAMINE DERIVATIVES CONTAINING A PYRROLIDYL GROUP, AND USE OF THESE DERIVATIVES FOR COLORING KERATIN FIBERS

(75) Inventors: Stéphane Sabelle, Paris (FR); Laure Ramos, Bourg Lareine (FR); Madeleine LeDuc, Paris (FR)

(73) Assignee: L'Oreal, Paris (FR)

( * ) Notice: Subject to any disclaimer, the term of this patent is extended or adjusted under 35 U.S.C. 154(b) by 288 days.

(21) Appl. No.: 10/612,986

(22) Filed: Jul. 7, 2003

(65) Prior Publication Data

US 2004/0077852 A1    Apr. 22, 2004

Related U.S. Application Data

(60) Provisional application No. 60/408,900, filed on Sep. 9, 2002.

(30) Foreign Application Priority Data

Jul. 5, 2002    (FR)    .................... 02 08514

(51) Int. Cl.
*A61Q 5/10* (2006.01)
*C07D 401/04* (2006.01)
*C07D 413/04* (2006.01)
*C07D 207/14* (2006.01)
*C07D 403/04* (2006.01)

(52) U.S. Cl. .............. 540/575; 8/405; 8/406; 8/409; 544/141; 544/372; 546/208; 548/262.2; 548/314.7; 548/364.1; 548/518; 548/557

(58) Field of Classification Search .......... 8/405, 8/406, 409; 540/575; 544/141, 372; 546/208; 548/262.2, 314.7, 364.1, 518, 557
See application file for complete search history.

(56) References Cited

U.S. PATENT DOCUMENTS

| 2,261,002 | A | 10/1941 | Ritter |
| 2,271,378 | A | 1/1942 | Searle |
| 2,273,780 | A | 2/1942 | Dittmar |
| 2,375,853 | A | 5/1945 | Kirby et al. |
| 2,388,614 | A | 11/1945 | Kirby et al. |
| 2,454,547 | A | 11/1948 | Bock et al. |
| 3,061,432 | A | 10/1962 | Menzel et al. |
| 3,206,462 | A | 9/1965 | McCarty |
| 3,227,554 | A | 1/1966 | Barr et al. |
| 3,419,391 | A | 12/1968 | Young |
| 3,725,067 | A | 4/1973 | Bailey et al. |
| 3,758,309 | A | 9/1973 | Bailey et al. |
| 3,874,870 | A | 4/1975 | Green et al. |
| 3,915,921 | A | 10/1975 | Schlatzer, Jr. |
| 3,926,631 | A | 12/1975 | Arai et al. |
| 3,929,990 | A | 12/1975 | Green et al. |
| 3,966,904 | A | 6/1976 | Green et al. |
| 4,001,432 | A | 1/1977 | Green et al. |
| 4,003,699 | A | 1/1977 | Rose et al. |
| 4,005,193 | A | 1/1977 | Green et al. |
| 4,025,617 | A | 5/1977 | Green et al. |
| 4,025,627 | A | 5/1977 | Green et al. |
| 4,025,653 | A | 5/1977 | Green et al. |
| 4,026,945 | A | 5/1977 | Green et al. |
| 4,027,020 | A | 5/1977 | Green et al. |
| 4,128,425 | A | 12/1978 | Greenwald |
| 4,157,388 | A | 6/1979 | Christiansen |
| 4,349,532 | A | 9/1982 | Vanlerberghe et al. |
| 4,390,689 | A | 6/1983 | Jacquet et al. |
| 4,500,548 | A | 2/1985 | Silva |
| 4,500,630 | A | 2/1985 | Sato et al. |
| 4,509,949 | A | 4/1985 | Huang et al. |
| 4,540,654 | A | 9/1985 | Sato et al. |
| 4,608,250 | A | 8/1986 | Jacquet et al. |
| 4,621,046 | A | 11/1986 | Sato et al. |
| 4,698,065 | A | 10/1987 | Hoeffkes et al. |
| 4,702,906 | A | 10/1987 | Jacquet et al. |
| 4,719,282 | A | 1/1988 | Nadolsky et al. |
| 4,823,985 | A | 4/1989 | Grollier et al. |
| 4,842,849 | A | 6/1989 | Grollier et al. |
| 4,996,059 | A | 2/1991 | Grollier et al. |
| 5,061,289 | A | 10/1991 | Clausen et al. |
| 5,135,543 | A | 8/1992 | Chan et al. |
| 5,196,189 | A | 3/1993 | Jacquet et al. |
| 5,249,740 | A | 10/1993 | Serra Tosio et al. |
| 5,256,526 | A | 10/1993 | Suzuki et al. |
| 5,278,034 | A | 1/1994 | Ohki et al. |
| 5,279,619 | A | 1/1994 | Cotteret et al. |
| 5,344,463 | A | 9/1994 | Chan et al. |
| 5,380,340 | A | 1/1995 | Neunhoeffer et al. |
| 5,441,863 | A | 8/1995 | Tang et al. |

(Continued)

FOREIGN PATENT DOCUMENTS

DE    23 59 399    6/1975

(Continued)

OTHER PUBLICATIONS

English language Derwent Abstract of EP 0 770 375, May 2, 1997.

(Continued)

*Primary Examiner*—Kamal A. Saeed
*Assistant Examiner*—Rebecca Anderson
(74) *Attorney, Agent, or Firm*—Finnegan, Henderson, Farabow, Garrett & Dunner, L.L.P.

(57) ABSTRACT

The invention relates to novel pyrrolidyl-substituted para-phenylenediamine derivatives, to dye compositions containing them and to the process for dyeing keratin fibers using these compositions.

The present invention makes it possible in particular to obtain a chromatic, strong, relatively unselective and resistant coloration of keratin fibers.

26 Claims, No Drawings

U.S. PATENT DOCUMENTS

| | | | |
|---|---|---|---|
| 5,457,210 A | 10/1995 | Kim et al. |
| 5,494,490 A | 2/1996 | Audousset et al. |
| 5,538,516 A | 7/1996 | Audousset et al. |
| 5,567,421 A | 10/1996 | Cotteret et al. |
| 5,690,696 A | 11/1997 | Bone et al. |
| 5,707,786 A | 1/1998 | Schmuck et al. |
| 5,708,151 A | 1/1998 | Mockli |
| 5,735,908 A | 4/1998 | Cotteret et al. |
| 5,766,576 A | 6/1998 | Lowe et al. |
| 5,769,903 A | 6/1998 | Audousset et al. |
| 5,785,717 A | 7/1998 | Maubru et al. |
| 5,851,237 A | 12/1998 | Anderson et al. |
| 5,863,300 A | 1/1999 | Audousset et al. |
| 5,876,464 A | 3/1999 | Lim et al. |
| 5,993,491 A | 11/1999 | Lim et al. |
| 6,042,620 A | 3/2000 | Braun et al. |
| 6,099,592 A | 8/2000 | Vidal et al. |
| 6,099,593 A | 8/2000 | Terranova et al. |
| 6,165,230 A | 12/2000 | Rose et al. |
| 6,379,396 B1 | 4/2002 | Audousset |
| 6,461,391 B1 | 10/2002 | Lim et al. |
| 6,464,731 B1 | 10/2002 | Genet et al. |
| 6,500,213 B1 | 12/2002 | Braun et al. |
| 6,521,761 B1 | 2/2003 | Lim et al. |
| 6,613,313 B1 | 9/2003 | Kimura |
| 6,638,321 B1 | 10/2003 | Genet et al. |
| 6,673,124 B1 | 1/2004 | Laurent et al. |
| 6,946,005 B1 * | 9/2005 | Sabelle et al. ............... 8/405 |
| 2002/0197223 A1 | 12/2002 | Kimura |
| 2003/0093866 A1 | 5/2003 | Vidal et al. |
| 2003/0150066 A1 | 8/2003 | Richard |
| 2004/0064902 A1 | 4/2004 | Sabelle et al. |
| 2004/0074013 A1 | 4/2004 | Terranova et al. |
| 2004/0078905 A1 | 4/2004 | Terranova et al. |
| 2004/0083559 A1 | 5/2004 | Sabelle et al. |
| 2004/0088799 A1 | 5/2004 | Sabelle et al. |

FOREIGN PATENT DOCUMENTS

| | | |
|---|---|---|
| DE | 38 43 892 | 6/1990 |
| DE | 41 33 957 | 4/1993 |
| DE | 42 34 886 A1 | 4/1994 |
| DE | 42 41 532 | 6/1994 |
| DE | 195 43 988 | 5/1997 |
| DE | 299 01 593 | 4/1999 |
| DE | 299 02 262 | 5/1999 |
| DE | 100 34 617 A1 | 1/2002 |
| EP | 0 119 860 | 9/1984 |
| EP | 0 122 324 | 10/1984 |
| EP | 0 173 109 | 3/1986 |
| EP | 0 216 479 | 4/1987 |
| EP | 0 244 160 | 11/1987 |
| EP | 0 285 274 | 10/1988 |
| EP | 0 304 001 | 2/1989 |
| EP | 0 456 226 | 11/1991 |
| EP | 0 488 248 | 6/1992 |
| EP | 0 4880909 | 6/1992 |
| EP | 0 518 238 | 12/1992 |
| EP | 0 557 851 | 9/1993 |
| EP | 0 578 248 | 1/1994 |
| EP | 0 714 954 | 6/1996 |
| EP | 0 770 375 | 5/1997 |
| EP | 0 943 614 A2 | 9/1999 |
| EP | 0 962 452 | 12/1999 |
| EP | 1 018 508 A1 | 7/2000 |
| FR | 1 400 366 | 4/1965 |
| FR | 2 075 583 | 10/1971 |
| FR | 2 270 846 | 12/1975 |
| FR | 2 316 271 | 1/1977 |
| FR | 2 320 330 | 3/1977 |
| FR | 2 336 434 | 7/1977 |
| FR | 2 413 907 | 8/1979 |
| FR | 2 586 913 | 3/1987 |
| FR | 2 733 749 | 11/1996 |
| FR | 2 750 048 | 12/1997 |
| FR | 2 766 178 A1 | 1/1999 |
| FR | 2 801 308 | 5/2001 |
| GB | 1 021 400 | 3/1966 |
| GB | 1 026 978 | 4/1966 |
| GB | 1026 978 | 4/1966 |
| GB | 1 153 196 | 5/1969 |
| GB | 1 458 377 | 12/1976 |
| GB | 1 597 034 | 9/1981 |
| GB | 2 239 265 | 6/1991 |
| JP | 54-062335 | 5/1979 |
| JP | 56-092812 | 7/1981 |
| JP | 58-42045 | 3/1983 |
| JP | 59-98437 | 6/1984 |
| JP | 59-99437 | 6/1984 |
| JP | 59-162548 | 9/1984 |
| JP | 59-171956 | 9/1984 |
| JP | 60-33552 | 2/1985 |
| JP | 60-43659 | 3/1985 |
| JP | 60-172982 | 9/1985 |
| JP | 60-190779 | 9/1985 |
| JP | 61-165315 | 7/1986 |
| JP | 62-279337 | 12/1987 |
| JP | 1-115048 | 5/1989 |
| JP | 2-19576 | 1/1990 |
| JP | 4-235909 | 8/1992 |
| JP | 5-163124 | 6/1993 |
| JP | 6-199642 | 7/1994 |
| JP | 6-236011 | 8/1994 |
| JP | 6-329522 | 11/1994 |
| JP | 7-36159 | 2/1995 |
| JP | 7-076509 | 3/1995 |
| JP | 7-84348 | 3/1995 |
| JP | 7-92632 | 4/1995 |
| JP | 7-98489 | 4/1995 |
| JP | 7-244361 | 9/1995 |
| JP | 7-267832 | 10/1995 |
| JP | 7-267835 | 10/1995 |
| JP | 7-325375 | 12/1995 |
| JP | 8-034714 | 2/1996 |
| JP | 8-231359 | 9/1996 |
| JP | 11-071247 | 3/1999 |
| JP | 11-158048 | 6/1999 |
| JP | 11-292745 | 10/1999 |
| WO | WO 94/08969 | 4/1994 |
| WO | WO 94/08970 | 4/1994 |
| WO | WO 95-01772 | 1/1995 |
| WO | WO 95/15144 | 6/1995 |
| WO | WO 96/15765 | 5/1996 |
| WO | WO 98/01106 | 1/1998 |
| WO | WO 98/01434 | 1/1998 |
| WO | WO 98/20847 | 5/1998 |
| WO | WO 98/38175 | 9/1998 |
| WO | WO 99/03819 | 1/1999 |
| WO | WO 99/11229 | 3/1999 |
| WO | WO 99/17725 | 4/1999 |
| WO | WO 99/64417 | 12/1999 |
| WO | WO 01/68043 | 9/2001 |
| WO | WO 02/45675 | 6/2002 |

OTHER PUBLICATIONS

English language Derwent Abstract of FR 2 801 308, May 25, 2001.
English language Derwent Abstract of JP 2-19576, Jan. 23, 1990.
English language Derwent Abstract of JP 5-163124, Jun. 29, 1993.
English language Derwent Abstract of JP 11-158048, Jun. 15, 1999.
Co-pending U.S. Appl. No. 09/959,913, filed Mar. 31, 2001.
Co-pending U.S. Appl. No. 10/397,245, filed Mar. 27, 2003.
Co-pending U.S. Appl. No. 10/433,408, filed Jun. 4, 2003.
Co-pending U.S. Appl. No. 10/433,411, filed Oct. 29, 2003.

Co-pending U.S. Appl. No. 10/433,687, filed Jun. 5, 2003.
Co-pending U.S. Appl. No. 10/433,688, filed Nov. 5, 2003.
Co-pending U.S. Appl. No. 10/433,689, filed Nov. 12, 2003.
Co-pending U.S. Appl. No. 10/603,831, filed Jun. 26, 2003.
Co-pending U.S. Appl. No. 10/657,245, filed Dec. 9, 2003.
E. Hannig et al., "Kurze Orginalmitteilungen", Die Parmazie, p. 231, 1980.
E.J. Browne et al., "Triazoles. Part VII.* Syntheses of Substituted 1,2,4-Triazoles", Journal of The Chemical Society, pp. 5149-5152, 1962.
English language Derwent Abstract of DE 100 34 617, Jan. 31, 2002.
English language Derwent Abstract of DE 195 43 988, May 28, 1997.
English language Derwent Abstract of DE 23 59 399, Jun. 12, 1975.
English language Derwent Abstract of DE 299 01 593, Apr. 8, 1999.
English language Derwent Abstract of DE 299 02 262, May 6, 1999.
English language Derwent Abstract of DE 38 43 892, Jun. 28, 1990.
English language Derwent Abstract of DE 41 33 957, Apr. 15, 1993.
English language Derwent Abstract of DE 42 34 886, Apr. 21, 1994.
English language Derwent Abstract of DE 42 41 532, Jun. 16, 1994.
English language Derwent Abstract of EP 0 943 614, Dec. 12, 2001.
English language Derwent Abstract of FR 2 320 330, Mar. 4, 1997.
English language Derwent Abstract of FR 2 336 434, Jul. 22, 1977.
English language Derwent Abstract of FR 2 586 913, Mar. 13, 1987.
English language Derwent Abstract of FR 2 733 749, Nov. 8, 1996.
English language Derwent Abstract of FR 2 750 048, Dec. 26, 1997.
English language Derwent Abstract of FR 2 766 178, Jan. 22, 1999.
English language Derwent Abstract of JP 1-115048, May 8, 1989.
English language Derwent Abstract of JP 58042045, Mar. 11, 1983.
English language Derwent Abstract of JP 5999437, Jun. 8, 1984.
English language Derwent Abstract of JP 60190779, Sep. 28, 1985.
English language Derwent Abstract of JP 6033552, Feb. 20, 1985.
English language Derwent Abstract of JP 6043659, Mar. 8, 1985.
English language Derwent Abstract of JP 62279337, Dec. 4, 1987.
English language Derwent Abstract of JP 6236011, Aug. 23, 1994.
English language Derwent Abstract of JP 7036159, Feb. 7, 1995.
English language Derwent Abstract of JP 7084348, Mar. 31, 1995.
English language Derwent Abstract of JP 7092632, Apr. 7, 1995.
English language Derwent Abstract of JP 7098489, Apr. 11, 1995.
English language Derwent Abstract of JP 7244361, Sep. 19, 1995.
English language Derwent Abstract of JP 7325375, Dec. 12, 1995.
Eser Ilhan, et al., "Synthese von 6-Benzyliden-2-(a,a-diphenyl-a-hydroxyacetyl)-thiazolo[3,2-b]-s-frialzol-5-onen als potentiell biologisch wirksame Stroffe", Archiv der Pharmazie, pp. 825-826, 1994.
French Search Report for FR 02/03847, Nov. 25, 2002.
French Search Report for FR 02/07939, Feb. 17, 2003.
French Search Report for FR 02/08514, Mar. 20, 2003.
French Search Report for FR 02/11133, May 15, 2003.
G. Fonnum et al., "'Associative thickeners. Part I: Synthesis, rheology and aggregation behavior", Colloid & Polymer Science, 271, pp. 380-389, 1993.
Giuliana Cardillo et al., "Sulle 1,2-difenil-3,5-dichetopirazolidine", Gazzetta Chimica Italiana, vol. 96, pp. 973-985, 1966.
H. Koopman, :"Investigations on Herbicides IV, The synthesis of 2,6-dichlorobenzonitrile", Recueil, pp. 1075-1083, 1961.
Hans Beyer et al., "Uber die Pyrazolbidung aus alpha-Chloracetessigester und Thiocarbohydrazid," Chemische Berichte, pp. 2550-2555, 1956.
Henryk Foks et al., "Synthesis and Biological Activity of Thiazolo-1,2,4-Triazoles", Acta Poloniae Pharmaceutica—Drug Research, pp. 415-420, 1995.
International Search Report for PCT/FR 01/00745, Sep. 14, 2001.
International Search Report for PCT/FR 01/03540, Mar. 11, 2002.
International Search Report for PCT/FR 01/03541, Mar. 11, 2002.
International Search Report for PCT/FR 01/03542, Mar. 11, 2002.
International Search Report for PCT/FR 01/03543, Mar. 14, 2002.
International Search Report for PCT/FR 01/03571, Mar. 11, 2002.
Joseph Bailey, "Synthesis of 1 H-Pyrazolo[3,2-c]-s-Triazoles and Derived Azamethine Dyes," Journal of The Chemical Society, pp. 2047-2052, 1977.

Lidia Wyzgowska, et al., "O Reakcjach Trikarboetoksymetanu", Acta Poloniae Pharmaceutica, pp. 83-88, 1982.
Mohamed Ali et al., "Reactions with Thiazolo[3,2-b]-s-triazol-3(2H)-ones", Journal Für Praktische Chemie, pp. 12-18, 1976.
Mohamed Elnagdi et al., "Routes for the Synthesis of 3,5-Diaminopyrazoles, 2-Aminopyrazolo[1,5-a]pyrimidines and 5-Aminopyrazolo[1,5-a]pyrimidines", Journal Für Praktische Chemie, pp. 533-538, 1978.
Mohamed Elnagdi et al., "Studies on 3,5-pyrazolidinediones. IV. Addition of 4-Arylazo-3,5-pyrazolidinediones to Ethyl Acrylate", Bulletin of the Chemical Society of Japan, vol. 46, 1973. pp. 1830-1833.
Office Action in co-pending U.S. Appl. No. 09/656,913, dated Dec. 14, 2004.
Office Action in co-pending U.S. Appl. No. 09/959,913, dated Dec. 16, 2003.
Office Action in co-pending U.S. Appl. No. 10/433,411, dated Sep. 9, 2004.
Office Action in co-pending U.S. Appl. No. 10/433/687, dated Sep. 14, 2004.
Office Action in co-pending U.S. Appl. No. 10/433,688, dated Feb. 10, 2005.
Office Action in co-pending U.S. Appl. No. 10/433,688, dated Sep. 9, 2004.
Office Action in co-pending U.S. Appl. No. 10/433,689, dated Oct. 26, 2004.
Paul Carter et al., "Studies on the Synthesis of the Antitumor Agent CC-1065. Synthesis of PDE I and PDE II, Inhibitors of Cyclic Adenosine-3',5'-monophosphate Phosphodiesterase Using the 3,3'-Bipyrrole Strategy", Journal of the American Chemical Society, pp. 2711-2717, 1987.
Philip Magnus et al., "Synthesis of Helical Poly-b-pyrroles. Multiple Atropisomerism Resulting in Helical Enantiomorphic Conformations", Journal of the American Chemical Society, pp. 2465-2468, 1990.
R. Stollé, "Ueber die Ueberführung der secundären Säurehydrazide in Derivate des Furodiazols, Pyrrodiazols und Thiodiazols", Berichte Der Deutschen Chemischen Gesellschaft, pp. 797-798, 1899.
R.L. Bent et al., "Chemical Constitution, Electrochemical, Photographic and Allergenic Properties of p-Amino-N-dialkylanilines," Journal of the American Chemical Society, vol. 73, No. 7, Jul. 1951, pp. 3100-3125.
S. Hiller et al., "Electron Density Distribution in Hetrocyclic Systems With Two Adjacent Nitrogen Atoms", Chemistry of Heterocyclic Compounds, pp. 93-96, 1965.
Thomas Kauffman et al., "Synthese von Amidrazonen aus Nitrilen und Natriumhydrazid", Chemische Berichte, pp. 3436-3443, 1964.
Victor Cohen, "A New Method of Synthesis of Some 2-Aryl and 2-Heterocyclic Benzimidazole, Benzoxazole and Benzothiazole Derivatives", Journal of Heterocyclic Chemistry, 16, pp. 13-16, 1979.
English language Derwent Abstract of JP 11-071247.
English language Derwent Abstract of JP 7-267832.
English language Derwent Abstract of JP 7-267835.
Office Action in co-pending U.S. Appl. No. 10/433,687 dated Apr. 8, 2005 (Ex. Elhilo).
Office Action in co-pending U.S. Appl. No. 10/433,687 dated Aug. 31, 2005 (Ex. Elhilo).
Office Action in co-pending U.S. Appl. No. 09/959,913 dated Jul. 18, 2005 (Ex. Elhilo).
Office Action in co-pending U.S. Appl. No. 09/959,913 dated Mar. 28, 2006 (Ex. Elhilo).
Office Action in co-pending U.S. Appl. No. 10/433,408 dated Jul. 5, 2005 (Ex. Elhilo).
Office Action in co-pending U.S. Appl. No. 10/433,411 dated Apr. 8, 2005 (Ex. Elhilo).
Office Action in co-pending U.S. Appl. No. 10/433,411 dated Aug. 31, 2005 (Ex. Elhilo).
Office Action in co-pending U.S. Appl. No. 10/433,689 dated Aug. 2, 2005 (Ex. Elhilo).

* cited by examiner

PARA-PHENYLENEDIAMINE DERIVATIVES CONTAINING A PYRROLIDYL GROUP, AND USE OF THESE DERIVATIVES FOR COLORING KERATIN FIBERS

This application claims benefit of U.S. Provisional Application No. 60/408,900, filed Sep. 9, 2002.

Disclosed herein are novel pyrrolidyl-substituted para-phenylenediamine derivatives. Also disclosed herein are dye compositions comprising the novel pyrrolidyl-substituted para-phenylenediamine derivatives and a process for dyeing keratin fibers using the dye compositions.

It is known practice to dye keratin fibers, for example, human hair, with dye compositions comprising oxidation dye precursors, for example, oxidation dye precursors chosen from ortho- and para-phenylenediamines; ortho- and para-aminophenols; and heterocyclic compounds (such as diamino-pyrazole derivatives, pyrazolo[1,5-a]pyrimidine derivatives, pyrimidine derivatives, pyridine derivatives, 5,6-dihydroxyindole derivatives and 5,6-dihydroxyindoline derivatives). Oxidation dye precursors, or oxidation bases, are colorless or weakly colored compounds which, when combined with oxidizing products, can give rise to colored compounds and dyes by a process of oxidative condensation.

It is also known that the shades obtained with oxidation bases may be varied by combining the oxidation bases with couplers or coloration modifiers. For example, coloration modifiers may be chosen from meta-phenylenediamines, meta-aminophenols, meta-hydroxyphenols and certain heterocyclic compounds, for instance pyrazolo[1,5-b]-1,2,4-triazole derivatives, pyrazolo[3,2-c]-1,2,4-triazole derivatives, pyrazolo[1,5-a]pyrimidine derivatives, pyridine derivatives, 5-pyrazolone derivatives, indoline derivatives and indole derivatives.

The variety of molecules that can be used as oxidation bases and couplers allows a wide range of colors to be obtained.

The "permanent" coloration obtained using these oxidation dyes must satisfy a certain number of requirements. For example, the oxidation dyes should not have toxicological drawbacks. In addition, oxidation dyes should produce shades in the desired intensity, and the shades should show good resistance to external agents (for instance, light, bad weather, washing, permanent-waving, perspiration and rubbing). Permanent oxidation dyes should also be able to cover grey hair and, should be as unselective as possible, i.e., ideally they should produce the smallest possible differences in coloration along the same length of a keratin fiber, which may in fact be differently sensitized (i.e., damaged) between its end and its root. It is also desired that oxidation dyes show good chemical stability in the formulations and have a good toxicological profile.

In the field of hair dyeing, para-phenylenediamine and para-tolylenediamine are oxidation bases that are widely used. They can produce varied shades with oxidation couplers.

However, there is a need to discover novel oxidation bases with a better toxicological profile than that of para-phenylenediamine and para-tolylenediamine, while at the same time being able to give the keratin fibers excellent properties in terms of at least one of: color intensity, variety of shades, color uniformity and resistance to external agents.

It is already known to use para-phenylenediamine derivatives substituted with a pyrrolidine group as oxidation bases for coloring keratin fibers. For example, U.S. Pat. No. 5,851,237 describes the use of 1-(4-aminophenyl)pyrrolidine derivatives optionally substituted on the benzene nucleus as replacements for para-phenylenediamine. U.S. Pat. No. 5,993,491 proposes the use of N-(4-aminophenyl)-2-hydroxymethylpyrrolidine derivatives optionally substituted on the benzene nucleus and on the pyrrolidine heterocycle in position 4 with a hydroxyl radical, as replacements for para-phenylenediamine. Patent application JP 11-158 048 proposes compositions containing at least one compound chosen from 4-aminoaniline derivatives optionally substituted on the benzene nucleus and one of the nitrogen atoms of which is included in a 5- to 7-membered carbon-based ring. patent application EP 1 200 052 describes dye compositions containing, as an oxidation base, para-phenylenediamine derivatives in which one of the amino groups forms a pyrrolidine ring substituted in position 3 with an amino group.

However, the previously disclosed compounds in the art may not give the hair a coloration equivalent in quality to that obtained with para-phenylenediamine or with para-tolylenediamine due to a lack of intensity and lack of uniformity of the color.

There is thus a real need for novel oxidation bases that simultaneously have a good toxicological profile and properties such that the compositions comprising the novel oxidation bases can give the hair excellent properties in terms of at least one of: color intensity, variety of shades, color uniformity and resistance with respect to various external attacking factors to which the hair may be subjected.

Thus, the present disclosure describes novel dye compositions that do not have the drawbacks of the oxidation bases of the prior art. These novel dye compositions for dyeing keratin fibers do not degrade the keratin fibers, while at the same time are capable of producing intense colorations in varied shades, which are relatively unselective, particularly resistant and show a good toxicological profile.

One embodiment of the invention is a compound chosen from para-phenylenediamine derivatives substituted with a pyrrolidyl group, wherein said pyrrolidyl-substituted para-phenylenediamine derivative is chosen from derivatives corresponding to formula (I), and the addition salts thereof,

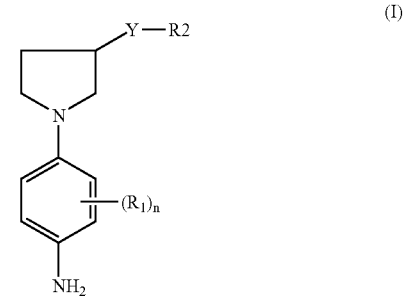

wherein:

n is an integer ranging from 0 to 4, provided that when n is greater than or equal to 2, then the radicals $R_1$ may be identical or different, $R_1$ is chosen from halogen atoms; saturated and unsaturated aliphatic and alicyclic $C_1$–$C_6$ hydrocarbon-based chains, wherein at least one carbon atom of the hydrocarbon-based chain may be replaced with at least one entity chosen from oxygen, nitrogen, silicon and sulphur atoms, and from SO and $SO_2$ groups, provided that the radical $R_1$ does not comprise a peroxide bond or a diazo, nitro or nitroso radical; and further wherein the hydrocarbon-based chain may be substituted with at least one group chosen from halogen atoms, hydroxyl, amino, mono-, di($C_1$–$C_4$)alkylamino and tri($C_1$–$C_4$)alkylammonium radicals;

Y is chosen from a covalent bond and a $C_1$–$C_{14}$ alkylene chain that may be linear or branched, wherein at least one carbon atom of the alkylene chain may be replaced with at least one atom chosen from oxygen, nitrogen and sulphur atoms, or with a group chosen from SO and $SO_2$ groups; wherein the alkylene chain may be substituted with at least one radical chosen from hydroxyl, $C_1$–$C_6$ alkoxy, amino, $C_1$–$C_6$ alkylamino and $C_1$–$C_6$ dialkylamino radicals; and further wherein the chain may bear at least one ketone functional group, $R_2$ is chosen from 3- to 7-membered saturated and unsaturated carbocycles and heterocycles, which may be substituted with at least one radical chosen from $C_1$–$C_6$ alkyl and $C_1$–$C_6$ hydroxyalkyl radicals.

Another embodiment disclosed herein is a dye composition comprising at least one pyrrolidyl-substituted para-phenylenediamine derivative chosen from the derivatives corresponding to formula (I) as an oxidation base.

Yet another embodiment disclosed herein is the use of the novel para-phenylenediamine derivatives to dye keratin fibers, as well as a process for dyeing keratin fibers, for instance, human keratin fibers such as the hair, using the composition comprising at least one pyrrolidyl-substituted para-phenylenediamine derivative chosen from derivatives corresponding to formula (I).

The dye composition comprising at least one one pyrrolidyl-substituted para-phenylenediamine derivative chosen from derivatives corresponding to formula (I) as disclosed herein can produce a chromatic, powerful, relatively unselective and resistant coloration of keratin fibers, and has a good toxicological profile.

In the context of the disclosure herein, an aliphatic hydrocarbon-based chain can be either a linear or branched chain that may contain unsaturations of the alkene or alkyne type. An alicyclic hydrocarbon-based chain is a branched chain containing a cyclic structure, which may contain one or more unsaturations of the alkene or alkyne type, but which does not contain an aromatic ring structure. When the carbon atoms of the chain are replaced with an entity, "T" chosen from oxygen, sulphur, nitrogen and silicon atoms, and from SO and $SO_2$ groups, a unit —T—$CH_2$— or —T— may be obtained.

By way of example, in one embodiment of the compound disclosed herein, $R_1$ may be chosen from chlorine atoms, bromine atoms, methyl, ethyl, isopropyl, vinyl, allyl, methoxymethyl, hydroxyethyl, 1-carboxymethyl, 1-aminomethyl, 2-carboxyethyl, 2-hydroxyethyl, 3-hydroxypropyl, 1,2-dihydroxyethyl, 1-hydroxy-2-aminoethyl, 1-amino-2-hydroxyethyl, 1,2-diaminoethyl, methoxy, ethoxy, allyloxy and 2-hydroxyethyloxy radicals.

In another embodiment of the compound disclosed herein, n is equal to 0 or 1.

According to yet another embodiment, $R_1$ is chosen from halogen atoms, $C_1$–$C_4$ alkyl radicals, $C_1$–$C_4$ hydroxyalkyl radicals, $C_1$–$C_4$ aminoalkyl radicals, $C_1$–$C_4$ alkoxy radicals and $C_1$–$C_4$ hydroxyalkoxy radicals. By way of example, $R_1$ may be chosen from methyl, hydroxymethyl, 2-hydroxyethyl, 1,2-dihydroxyethyl, methoxy, isopropyloxy and 2-hydroxyethoxy radicals.

In yet another embodiment of the compound disclosed herein, when Y is a covalent bond, then $R_2$ is directly linked to the pyrrolidine ring. In still another embodiment, when Y is an alkylene chain, then for example, Y may be chosen from $C_1$–$C_8$ alkylene chains that may comprise one or more units chosen from —O—, —NR'— and —NR'CO—, wherein R' is chosen from hydrogen atoms or $C_1$–$C_4$ alkyl radicals. Y may also be an entity chosen from: —O—, —NR'—, —S—, —SO— and —$SO_2$.

By way of another example, the radical $R_2$ may be a ring chosen from imidazole, pyrrolidine, piperazine, piperidine, triazole, diazepan, pyrazole, morpholine, tetrazole, furan, thiophene, pyrrole, oxazole, thiazole, and all the corresponding rings obtained by reducing at least one double bond of the rings thereof. As a further example, the triazole rings may be chosen from 1,2,3-triazole and 1,2,4-triazole rings.

According to another embodiment of the compound disclosed herein, $R_2$ is a nitrogenous heterocycle. For example, $R_2$ may be chosen from imidazole, pyrrolidine, piperazine, piperidine, triazole, diazepan and pyrazole rings. According to still another embodiment, $R_2$ may be linked to Y via one of the nitrogen atoms of the nitrogenous heterocycle. In an additional embodiment, when $R_2$ is a carbocycle, $R_2$ may be chosen from $C_4$–$C_7$ cycloalkyls and aryl radicals, for example, phenyl.

The compounds chosen from derivatives corresponding to formula (I) may be in the form of acid salts with strong mineral acids, for instance HCl, HBr and $H_2SO_4$, or with organic acids, for instance acetic acid, lactic acid, tartaric acid, citric acid and succinic acid.

Examples of further embodiments of derivatives of formula (I) that may be mentioned include:

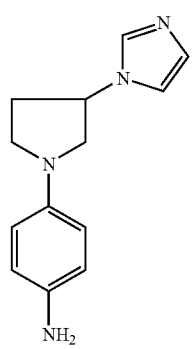

4-(3-Imidazol-1-ylpyrrolid-1-yl)phenylamine

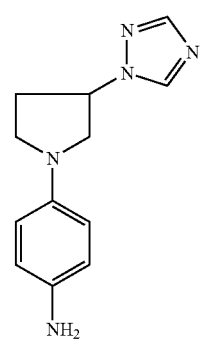

4-(3-[1,2,4]Triazol-1-ylpyrrolid-1-yl)phenylamine

-continued

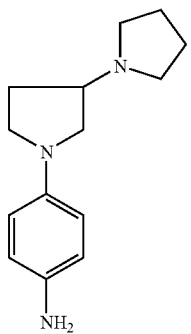
4-[1,3']Bipyrrolidyl-1'-ylphenylamine

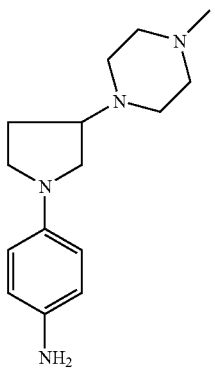
4-[3-(4-Methyl-piperazin-1-yl)-pyrrolid-1-yl]-phenylamine

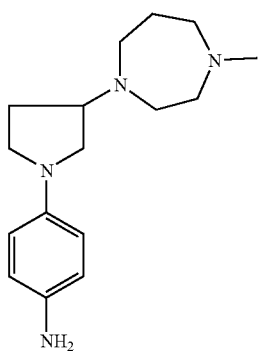
4-[3-(4-Methyl-[1,4]diazepan-1-yl)pyrrolid-1-yl]phenylamine

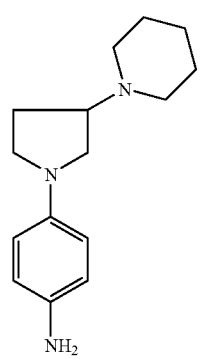
4-[3-(Piperid-1-yl)pyrrolid-1-yl]phenylamine

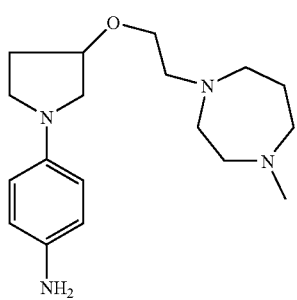
4-{3-[2-(4-Methyl[1,4]diazepan-1-yl)-ethoxy]pyrrolid-1-yl}phenylamine

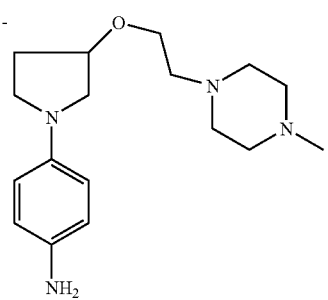
4-{3-[2-(4-Methylpiperazin-1-yl)ethoxy]pyrrolid-1-yl}phenylamine

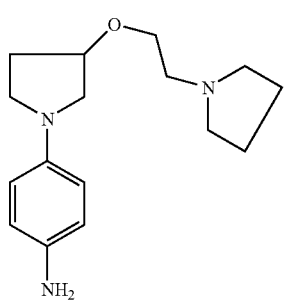
4-[3-(2-Pyrrolid-1-ylethoxy)pyrrolid-1-yl]phenylamine

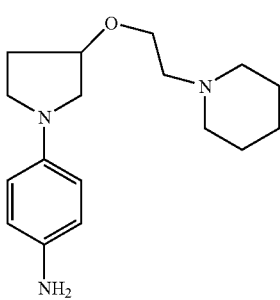
4-[3-(2-Piperid-1-ylethoxy)pyrrolid-1-yl]phenylamine

-continued

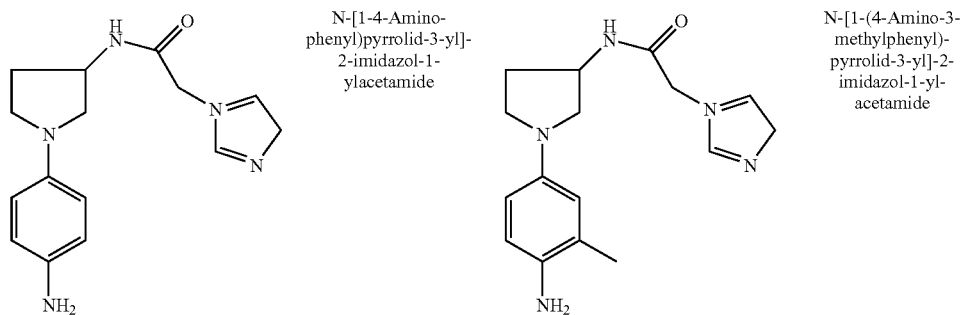

N-[1-4-Amino-phenyl)pyrrolid-3-yl]-2-imidazol-1-ylacetamide

N-[1-(4-Amino-3-methylphenyl)-pyrrolid-3-yl]-2-imidazol-1-yl-acetamide

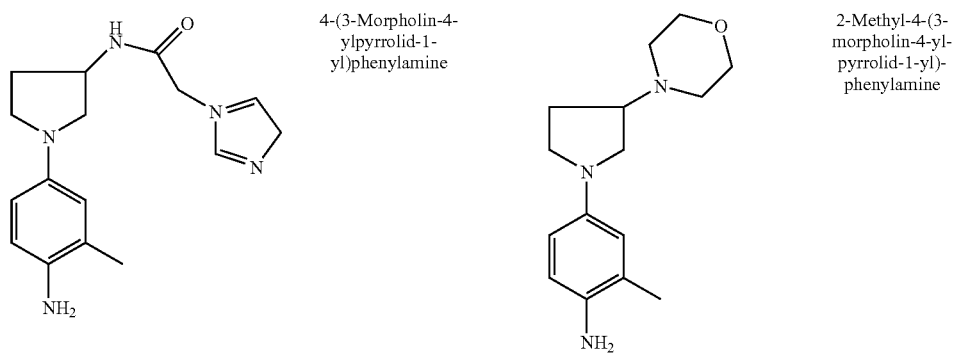

4-(3-Morpholin-4-ylpyrrolid-1-yl)phenylamine

2-Methyl-4-(3-morpholin-4-yl-pyrrolid-1-yl)-phenylamine

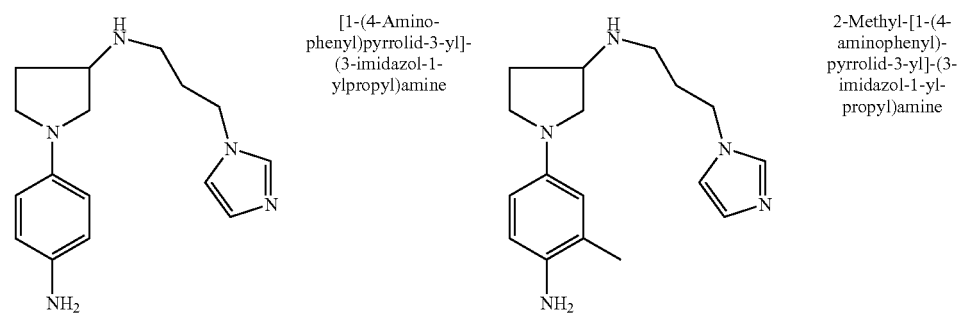

[1-(4-Amino-phenyl)pyrrolid-3-yl]-(3-imidazol-1-ylpropyl)amine

2-Methyl-[1-(4-aminophenyl)-pyrrolid-3-yl]-(3-imidazol-1-yl-propyl)amine

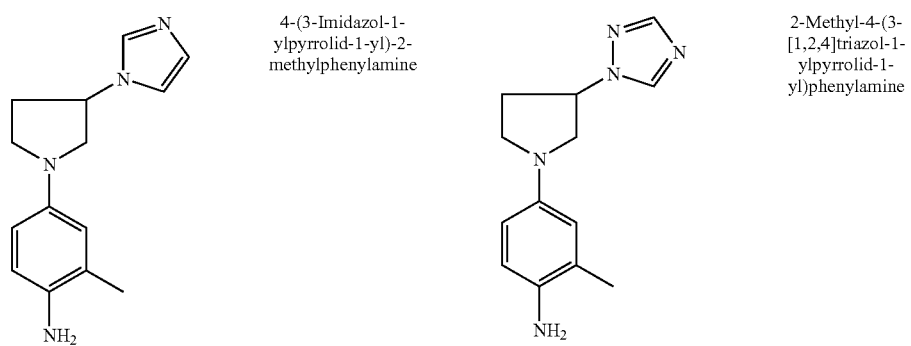

4-(3-Imidazol-1-ylpyrrolid-1-yl)-2-methylphenylamine

2-Methyl-4-(3-[1,2,4]triazol-1-ylpyrrolid-1-yl)phenylamine

-continued

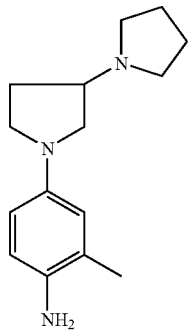
4-[1,3']Bipyrrolidyl-1'-yl-2-methylphenyl-amine

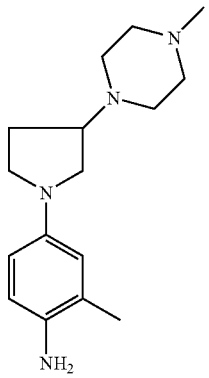
2-Methyl-4-[3-(4-methylpiperazin-1-yl)pyrrolid-1-yl]phenylamine

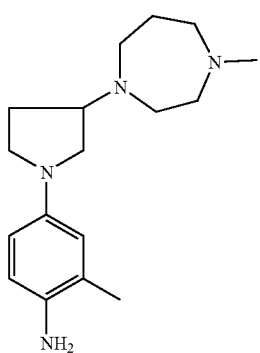
2-Methyl-4-[3-(4-methyl[1,4]diazepan-1-yl)pyrrolid-1-yl]phenylamine

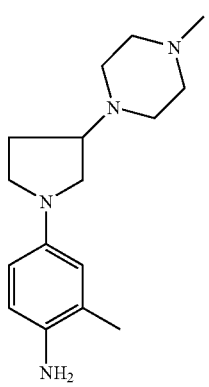
2-Methyl-4-[3-(piperid in-1-yl)-pyrrolid-1-yl]-phenylamine

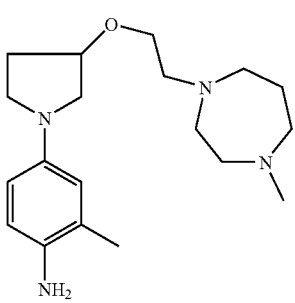
2-Methyl-4-{3-[2-(4-methyl[1,4]diazepan-1-yl)ethoxy]pyrrolid-1-yl}phenylamine

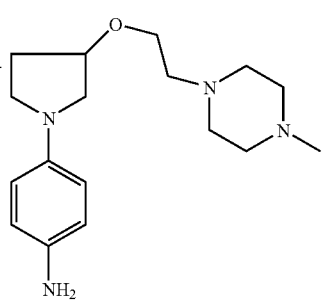
2-Methyl-4-{3-[2-(4-methylpiperazin-1-yl)ethoxy]pyrrolid-1-yl}phenylamine

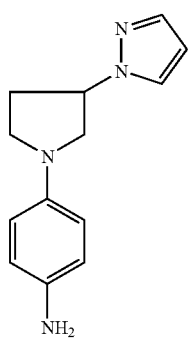
4-(3-Pyrazol-1-yl-pyrrolid-1-yl)-phenylamine

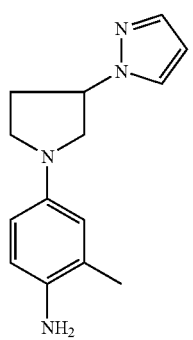
2-Methyl-4-(3-pyrazol-1-ylpyrrolid-1-yl)phenylamine

-continued

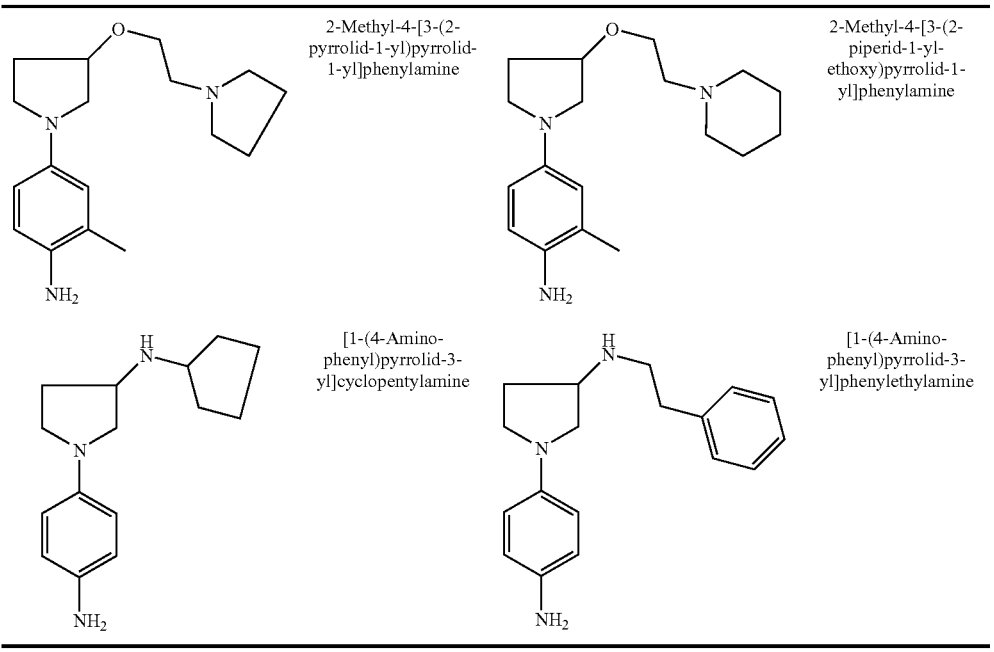

Among these compounds, the following compounds may be mentioned:
4-(3-lmidazol-1-ylpyrrolid-1-yl)phenylamine
4-[1,3']Bipyrrolid-1'-ylphenylamine
4-[3-(4-Methylpiperazin-1-yl)pyrrolid-1-yl]phenylamine
4-{3-[2-(4-Methylpiperazin-1-yl)ethoxy]pyrrolid-1-yl}phenylamine
4-[3-(2-Pyrrolid-1-ylethoxy)pyrrolid-1-yl]phenylamine
4-[3-(Piperidin-1-yl)pyrrolid-1-yl]phenylamine
4-[3-(2-Piperid-1-ylethoxy)pyrrolid-1-yl]phenylamine
[1-(4-Aminophenyl)pyrrolid-3-yl](3-imidazol-1-ylpropyl)amine
2-Methyl-[1-(4-aminophenyl)pyrrolid-3-yl]-(3-imidazol-1-ylpropyl)amine
4-(3-lmidazol-1-ylpyrrolid-1-yl)-2-methylphenylamine
4-[1,3']Bipyrrolid-1'-yl-2-methylphenylamine
2-Methyl-4-[3-(4-methylpiperazin-1-yl)pyrrolid-1-yl]phenylamine
2-Methyl-4-[3-(piperidin-1-yl)pyrrolid-1-yl]phenylamine
2-Methyl-4-{3-[2-(4-methylpiperazin-1-yl)ethoxy]pyrrolid-1-yl}phenylamine
4-(3-Pyrazol-1-ylpyrrolid-1-yl)phenylamine
2-Methyl-4-(3-pyrazole l-1-ylpyrrolid-1-yl)phenylamine
2-Methyl-4-[3-(2-pyrrolid-1-ylethoxy)pyrrolid-1-yl]phenylamine
2-Methyl-4-[3-(2-piperid-1-ylethoxy)pyrrolid-1-yl] phenylamine.

The dye composition as disclosed herein comprises, in a cosmetically acceptable medium that is suitable for dyeing keratin fibers, for example, human keratin fibers, at least one oxidation base comprising at least one pyrrolidyl-substituted para-phenylenediamine derivative chosen from derivatives corresponding to formula (I) as defined above.

The at least one oxidation base as disclosed above can be present in the dye composition an amount approximately ranging from 0.001% to 10%, by weight of each oxidation base, relative to the total weight of the dye composition. For example, the at least one oxidation base my be present in an amount approximately ranging from 0.005% to 6% by weight of each oxidation base, relative to the total weight of the dye composition.

The dye composition disclosed herein may also comprise at least one coupler conventionally used for dyeing keratin fibers. For example, the at least one coupler may be chosen from meta-phenylenediamines, meta-aminophenols, meta-diphenols, naphthalene-based couplers and heterocyclic couplers, and the addition salts thereof.

Further examples of couplers that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)-amino-3,4-methylenedioxybenzene and 2,6-bis(β-hydroxyethylamino)toluene and the acid addition salts thereof.

In the dye composition disclosed herein, the optional at least one coupler may be present in an amount ranging approximately from 0.001% to 10% by weight, relative to the total weight of the dye composition. For example the at least one coupler may be present in an amount ranging approximately from 0.005% to 6% by weight, relative to the total weight of the dye composition.

The dye composition disclosed herein may also comprise at least one additional oxidation base conventionally used in oxidation dyeing. By way of example, these additional oxidation bases can be chosen from para-phenylenediamines other than those described above, bis(phenyl)alkylenediamines, para-aminophenols, bis-para-aminophenols, ortho-aminophenols, heterocyclic bases, and the addition salts thereof.

For further example, mention may be made of para-phenylenediamines chosen from: para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the acid addition salts thereof.

Among the para-phenylenediamines mentioned above, further mention may be made of para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid addition salts thereof.

Examples of bis(phenyl)alkylenediamines that may be mentioned, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-amino-phenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and the acid addition salts thereof.

Examples of para-aminophenols that may be mentioned, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and the acid addition salts thereof.

Examples of ortho-aminophenols that may be mentioned, are 2-aminophenol, 2-amino-5-methylphenol, 2-amino-6-methylphenol, 5-acetamido-2-aminophenol, and the acid addition salts thereof.

Examples of heterocyclic bases that may be mentioned, are pyridine derivatives, pyrimidine derivatives and pyrazole derivatives.

Examples of pyridine derivatives that may be mentioned are the compounds described, in patents GB 1 026 978 and GB 1 153 196, such as 2,5-diaminopyridine; as well as 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid addition salts thereof.

Other pyridine oxidation bases that may be useful in the dye composition disclosed herein are 3-aminopyrazolo[1,5-a]pyridine oxidation bases and the addition salts thereof described, for example, in patent application FR 2 801 308. By way of example, mention may be made of pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid; 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2-(3-aminopyrazolo[1,5-a]pyrid-7-yl)ethanol; (3-aminopyrazolo[1,5-a]pyrid-2-yl)-methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxyethyl)amino]ethanol; 2-[(3-aminopyrazolo[1,5-a]pyrid-7-yl)(2-hydroxyethyl)amino]ethanol; 3-aminopyrazolo[1,5-a]-pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol; and the addition salts thereof with an acid or with a base.

Additional examples of pyrimidine derivatives that may be mentioned are the compounds described, for instance, in patents DE 2 359 399; JP 88-169 571; JP 05-63124; EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine. Further mention may be made of pyrazolopyrimidine derivatives, such as those mentioned in patent application FR-A-2 750 048, for example, pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-arminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyramidin-3-yl)(2-hydroxy-ethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]-pyrimidine, the acid addition salts thereof, and the tautomeric forms thereof, when a tautomeric equilibrium exists.

Examples of pyrazole derivatives that may be mentioned are the compounds described in patents DE 3 843 892 and DE 4 133 957 and patent applications WO 94/08969, WO 94/08970, FR-A-2 733 749 and DE 195 43 988, for instance, 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenyl pyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino- 1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, and the acid addition salts thereof.

The optional at least one additional oxidation base present in the dye composition disclosed herein can be present in the composition in an amount ranging approximately from 0.001% to 10%, by weight relative, for each additional oxidation base, to the total weight of the dye composition. For example, the at least one additional oxidation base may be present in the dye composition in an amount ranging approximately from 0.005% to 6% by weight relative, for each additional oxidation base, to the total weight of the dye composition.

In general, the addition salts of the oxidation bases and of the couplers that may be used in the dye composition disclosed herein are chosen from the acid addition salts, such as the hydrochlorides, hydrobromides, sulphates, citrates, succinates, tartrates, lactates, tosylates, benzenesulphonates, phosphates and acetates, and the base addition salts, such as sodium hydroxide, potassium hydroxide, ammonia, amines and alkanolamines.

In another embodiment, the dye composition may also comprise at least one direct dye that may be chosen from nitrobenzene dyes, azo direct dyes and methine direct dyes. The direct dyes may be of nonionic, anionic or cationic nature.

A medium that is suitable for dyeing, also known as the dye support, generally comprises water or a mixture of water and at least one organic solvent to dissolve the compounds which would not be sufficiently soluble in water. Examples of organic solvents that may be used are $C_1$–$C_4$ lower alkanols, (such as ethanol and isopropanol); polyols and polyol ethers (such as 2-butoxyethanol, propylene glycol, propylene glycol monomethyl ether, diethylene glycol monoethyl ether and monomethyl ether), and aromatic alcohols (such as benzyl alcohol or phenoxyethanol), and mixtures thereof.

The organic solvents may be present in the dye composition in proportions ranging approximately from 1% to 40% by weight, relative to the total weight of the dye composition; for example, ranging approximately from 5% to 30% by weight, relative to the total weight of the dye composition.

The dye composition as disclosed herein can also contain at least one of various adjuvants conventionally used in compositions for dyeing the hair, such as anionic, cationic, nonionic, amphoteric and zwitterionic surfactants, and mixtures thereof; anionic, cationic, nonionic, amphoteric and zwitterionic polymers, and mixtures thereof; inorganic and organic thickeners, for example, anionic, cationic, nonionic and amphoteric associative polymeric thickeners; antioxidants; penetration agents; sequestering agents; fragrances; buffers; dispersing agents; packaging agents such as, for example, silicones, which may or may not be volatile or modified; film-forming agents; ceramides; preserving agents and opacifiers.

The at least one adjuvant may be present in the dye composition in an amount ranging approximately from 0.01% to 20% by weight relative, for each adjuvant, to the weight of the composition.

Needless to say, a person skilled in the art will take care to select any of the optional additional compounds described above such that the advantageous properties intrinsically associated with the oxidation dye as disclosed herein are not, or are not substantially, adversely affected by the addition(s) envisaged.

The pH of the dye composition as disclosed herein, may range approximately from 3 to 12 and, for example, can range approximately from 5 to 11. It may be adjusted to the desired value using acidifying or basifying agents usually used in the dyeing of keratin fibers, or alternatively using standard buffer systems.

Among the acidifying agents that may be mentioned, for example, are inorganic and organic acids such as hydrochloric acid; orthophosphoric acid; sulphuric acid; carboxylic acids such as acetic acid tartaric acid, citric acid and lactic acid; and sulphonic acids.

Among the basifying agents that may bementioned, for example, are aqueous ammonia, alkaline carbonates, alkanolamines such as mono-, di- and triethanolamine and derivatives thereof, sodium hydroxide, potassium hydroxide and the compounds of formula (II) below:

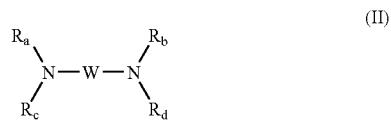

wherein W is a propylene residue that can be unsubstituted or substituted with an entity chosen fromhydroxyl groups and $C_1$–C4 alkyl radicals; $R_a$, $R_b$, $R_c$ and $R_d$, which may be identical or different, are each chosen from hydrogen atoms, $C_1$–$C_4$ alkyl radicals, and $C_1$–$C_4$ hydroxyalkyl radicals.

The dye composition as disclosed herein may be in various forms, such as liquids, creams and gels, or in any other form that is suitable for dyeing keratin fibers, for example human hair.

Also disclosed herein is a process for dyeing keratin fibers by of applying the dye composition as defined above to keratin fibers, in the presence of an oxidizing agent for a time that is sufficient to develop the desired coloration. The color may be developed at acidic, neutral and alkaline pH. The oxidizing agent may be mixed with the composition of the invention just at the time of use, or it may be used starting with an oxidizing composition comprising it, which can be applied simultaneously or sequentially to the dye composition of the invention.

According to one embodiment, the dye composition as described above is mixed, for example, at the time of use, with a composition comprising, in a medium that is suitable for dyeing, at least one oxidizing agent, this oxidizing agent being present in an amount that is sufficient to develop a coloration. The mixture obtained is then applied to the keratin fibers. After an action time ranging approximately from 3 to 50 minutes, for example, ranging approximately from 5 to 30 minutes, the keratin fibers are rinsed, washed with shampoo, rinsed again and then dried.

The oxidizing agents conventionally used for the oxidation dyeing of keratin fibers are, for example, hydrogen peroxide, urea peroxide, alkali metal bromates, persalts (such as perborates and persulphates), peracids and oxidase enzymes, among which mention may be made of peroxidases, 2-electron oxidoreductases such as uricases, and 4-electron oxygenases, for instance laccases. In one embodiment of the oxidizing composition disclosed herein, hydrogen peroxide is the oxidizing agent.

The oxidizing composition may also contain at least one adjuvant conventionally used in compositions for dyeing the hair and as defined above.

The pH of the oxidizing composition comprising the oxidizing agent is such that, after mixing with the dye composition, the pH of the resulting composition applied to the keratin fibers ranges approximately from 3 to 12, for example, the pH can range approximately from 5 to 11. It may be adjusted to the desired value by means of acidifying or basifying agents usually used in the dyeing of keratin fibers and as defined above.

The ready-to-use dye composition that is finally applied to the keratin fibers may be in various forms, such as in the form of liquids, creams or gels or any other form that is suitable for dyeing keratin fibers, for instance, human hair.

Another embodiment disclosed herein is a multi-compartment dyeing device or "kit", in which a first compartment contains the dye composition of the present invention defined above and a second compartment contains an oxidizing agent. This device may be equipped with a means for applying the, desired mixture to the hair, such as the devices described in patent FR-2 586 913, assigned to L'Oréal.

Using this device, it is possible to dye keratin fibers using a process that involves mixing a dye composition comprising at least one oxidation base comprising at least one pyrrolidyl-substituted para-phenylenediamine derivative chosen from derivatives corresponding to formula (I), with an oxidizing agent, and applying the mixture obtained to the keratin fibers for a time that is sufficient to develop the desired coloration.

The examples that follow serve to illustrate the invention without, however, being limiting in nature.

EXAMPLES

SYNTHESIS EXAMPLES

Example 1

Synthesis of 4-(3-imidazolyl-1-ylpyrrolid-1-yl)phenylamine

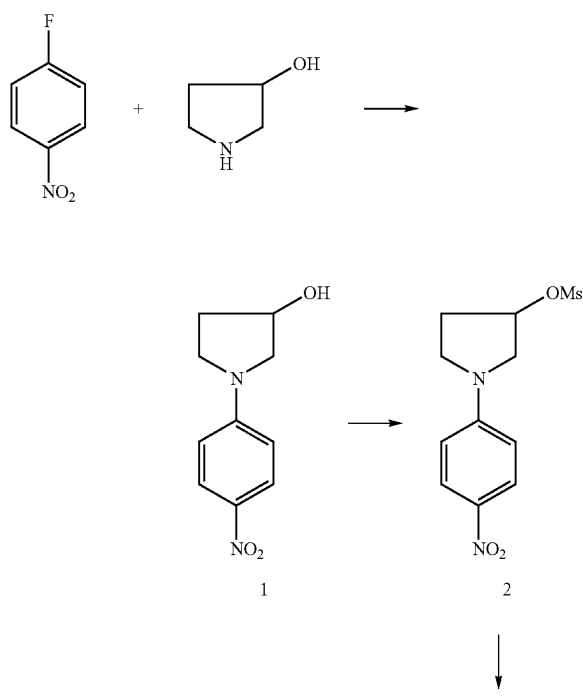

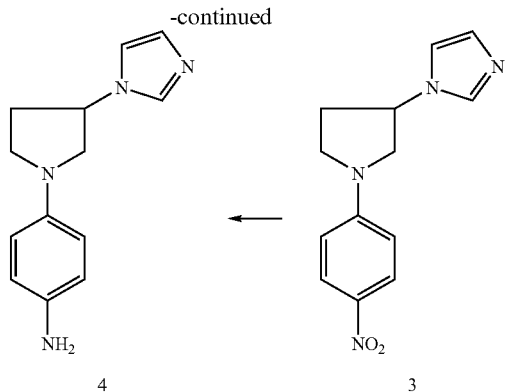

I. Synthesis of 1-(4-nitrophenyl)pyrrolid-3-yl methanesulphonate (2)

40 ml (0.516 mol) of mesyl chloride were added dropwise at 5° C. to 83.3 g (0.4 mol) of N-(4-nitrophenyl)-3-hydroxypyrrolidine dissolved in 625 ml of anhydrous THF and 72.7 ml (0.6 mol) of triethylamine. The mixture was allowed to return to room temperature and was then poured into ice to form a precipitate.

After suction-filtration and drying of the precipitate, 109 g of yellow powder (2) were obtained.

Melting point=203° C. $^1$H NMR (400 MHZ-DMSO) ppm 8.09 (d, 2H); 6.68 (d, 2H); 5.47 (m, 1H); 3.77–3.48 (m, 4H); 3.28 (s, 3H); 2.35 (m, 2H).

II. Synthesis of 1-[1-(4-nitrophenyl)pyrrolid-3-yl]-1H-imidazole (3)

22 g (0.0767 mol) of 1-(4-nitrophenyl)pyrrolid-3-yl methanesulphonate (2) were heated at 95° C. for 2 hours in 170 g of imidazole (2.5 mol), This mixture was poured into 1 l of ice-cold water until crystallization takes place. After filtration and drying, the yellow powder obtained was chromatographed, eluting with dichloromethane, and 14.5 g of derivative (3) were recovered (73.2% yield).

Melting point=163° C. $^1$H NMR (400 MHz-DMSO) ppm 8.20 (m, 2H); 7.87 (s, 1H); 7.38 (s, 1H); 7.06 (s, 1H); 6.81 (m, 2H); 5.17 (m, 1H); 4.06 (m, 1H); from 3.79 to 3.65 (m, 3H); 2.66 (m, 1H); 2.50 (m, 1H); Mass ESI+: m/z=259 [M+]

III. Synthesis of 4-(3-imidazolyl-1-ylpyrrolid-1-yl)phenylamine hydrochloride (4)

13.5 g (0.0522 mol) of the above derivative dissolved in 700 ml of ethanol were hydrogenated in the presence of palladium on charcoal under a hydrogen pressure of 8 bar. After filtering off the catalyst, the expected derivative (4) was isolated. in the form of the hydrochloride. 13 g of white powder are obtained; 82.7% yield.

$^1$H NMR (400 MHz-DMSO) ppm 9.29 (s, 1H); 7.84 (t, 1H); 7.71 (t, 1H); 7.26 (m, 2H); 6.67 (m, 2H); 5.29 (m, 1H); 3.77 (m, 1H); 3.68 (m, 2H); 3.38 (m, 1H); 2.51 (m, 1H); 246 (m, 1H); Mass ESI+: m/z=229 [M+]

Eample 2

Synthesis of 4-([1,3']bipyrrolinyl-1'-yl)phenylamine

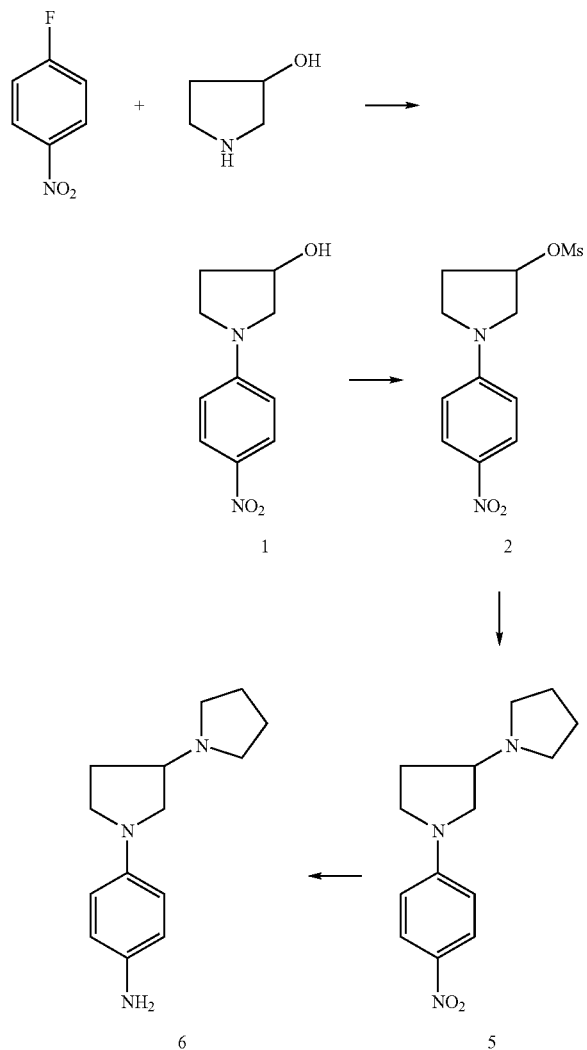

I. Synthesis of 1'-(4-nitrophenyl)[1,3]bipyrrolidinyl (5)

5 g (0.0174 mol) of 1-(4-nitrophenyl)pyrrolid-3-yl methanesulphonate (2) were heated at 85° C. for 2 hours in 30 ml of pyrrolidine (mol). This mixture was poured into ice-cold water until crystallization takes place. After filtration and drying, the yellow powder obtained was chromatographed, eluting with dichloromethane/methanol (98/2), and 2.6 g of derivative (5) were recovered (53% yield).

Melting point=114° C. $^1$H NMR (400 MHz-DMSO) ppm 8.04 (m, 2H); 6.61 (m, 2H); 3.60 (m, 2H); 3.40 (m, 1H); 3.24 (m, 1H); 2.86 (m, 1H); 2.50 (m, 2H); 2.16 (m, 1H); 1.92 (m, 1H); 1.70 (m, 4H). Mass ESI+: m/z=262 [M+]

II. Synthesis of 4-([1,3']bipyrrolinyl-1'-yl)phenylamine hydrochloride (6)

2.5 g (0.0096 mol) of the above derivative (5) dissolved in 400 ml of ethanol were hydrogenated in the presence of palladium on charcoal under a hydrogen pressure of 8 bar at a temperature of 50° C.; after filtering off the catalyst, the expected derivative (6) was isolated in the form of the hydrochloride. 1.3 g of a white powder are obtained; 44% yield.

$^1$H NMR (400 MHz-D$_2$O) ppm 7.33 (m, 2H); 6.86 (m, 2H); 4.11 (m, 1H); 3.75 (m, 3H); 3.60 (m, 2H); 3.39 (m, 1H); 2.60 (m, 1H); 2.31 (m, 1H); 2.18 (m, 2H); 2.06 (m, 2H). Mass ESI+: m/z=232 [M+]

Example 3

Synthesis of [1-(4-aminophenyl)pyrrolid-3-yl](3-imidazol-1-ylpropyl)amine

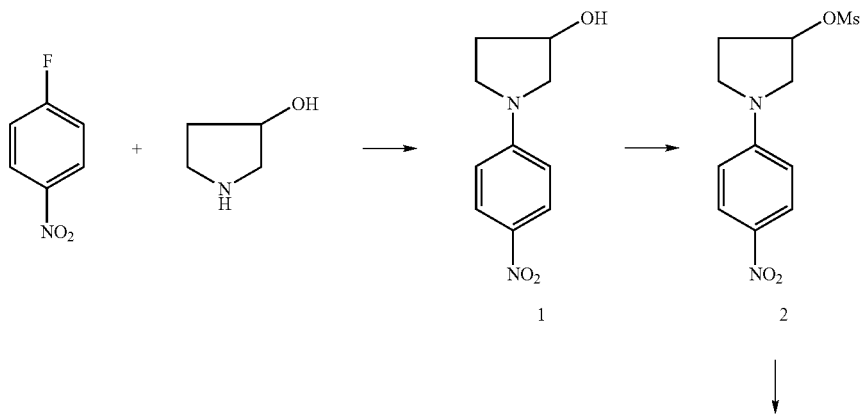

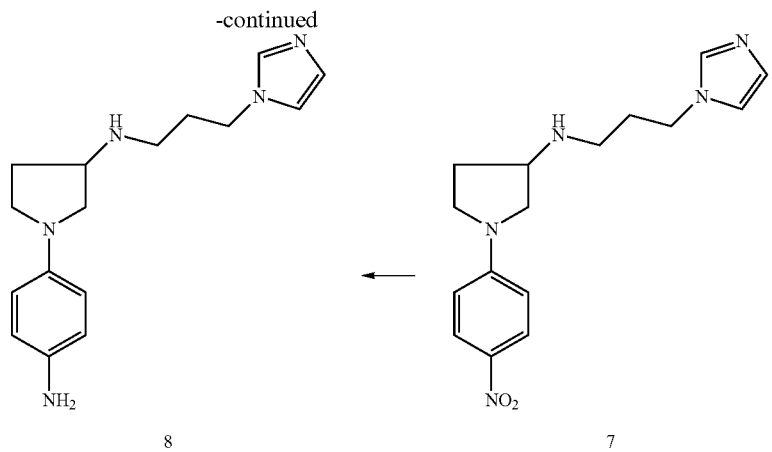

I. Synthesis of [3-(imidazol-1-yl)propyl][1-(4-nitrophenyl)pyrrolid-3-yl]amine (7)

30 g (0.105 mol) of 1-(4-nitrophenyl)pyrrolid-3-yl methylsulphonate (2) were heated at 90° C. for 18 hours with 120 g of aminopropylimidazole (0.958 mol). This mixture was poured into ice-cold water and the product was extracted with dichloromethane. The yellow powder obtained was chromatographed, eluting with dichloromethane/methanol (98/2), and 15.2 g of derivative (7) were recovered (48.2% yield).

Melting point=74° C. $^1$H NMR (400 MHz-DMSO) ppm 8.06 (m, 2H); 7.60 (s, 1H); 7.15 (s, 1H); 6.84 (s, 1H); 6.61 (m, 2H); 4.35 (bs, 1H); 4.03 (m, 2H); 3. (m, 2H); 3.49 (m, 2H); 3.24 (m, 1H); 2.15 (m, 1H); 1.85 (m, 3H). Mass ESI+: m/z=316 [M+]

II. Synthesis of [1-(4-aminophenyl)pyrrolid-3-yl]1 (3-imidazol-1-ylpropyl)amine hydrochloride (8)

6.5 g (0.0206 mol) of the above derivative (7) dissolved in 500 ml of ethanol were hydrogenated in the presence of palladium on charcoal, under 10 bar; after filtering off the catalyst, the expected derivative (8) was isolated in the form of the hydrochloride. 7.07 g of white powder are obtained; 86% yield.

$^1$H NMR (400 MHz-D$_2$O) ppm 8.86 (s, 1H); 7.63 (d, 1H); 7.55 (d, 1H); 7.34 (d, 2H); 6.83 (d, 2H); 4.46 (t, 1H); 4.13 (m, 1H); 3.72 (m, 1H); 3.61 (m, 2H); 3.40 (m, 1H); 2.58 (m, 1H);2.43 (m, 1H); 2.31 (m, 1H). Mass ESI+: m/z=286 [M+]

EXAMPLES OF DYEING

Examples 1 to 11

Dyeing in Alkaline Medium

| | Examples | | | | | | | | | | |
|---|---|---|---|---|---|---|---|---|---|---|---|
| | 1 | 2 | 3 | 4 | 5 | 6 | 7 | 8 | 9 | 10 | 11 |
| 4-(3-Imidazol-1-yl-pyrrolid-1-yl)phenylamine (base) | $10^{-3}$ | $10^{-3}$ | $10^{-3}$ | $10^{-3}$ | — | — | — | — | — | — | — |
| [1-(4-Aminophenyl)pyrrolid-3-yl](3-imidazol-1-ylpropyl)amine (base) | — | — | — | — | $10^{-3}$ | $10^{-3}$ | $10^{-3}$ | — | — | — | — |
| 4-[1,3']Bipyrrolid-1'-ylphenylamine (base) | — | — | — | — | — | — | — | $10^{-3}$ | $10^{-3}$ | $10^{-3}$ | $10^{-3}$ |
| 2-(2,4-Diaminophenoxy)ethanol dihydrochloride (coupler) | $10^{-3}$ | — | — | — | $10^{-3}$ | — | $10^{-3}$ | — | — | — | — |
| 3-Amino-2-chloro-6-methylphenol hydrochloride (coupler) | — | $10^{-3}$ | — | — | — | — | — | — | $10^{-3}$ | — | — |
| 3,6-Dimethyl-1H-pyrazolo[5,1-c][1,2,4]triazole (coupler) | — | — | $10^{-3}$ | — | — | $10^{-3}$ | — | — | — | $10^{-3}$ | — |
| 2-methyl-5-aminophenol (coupler) | — | — | — | $10^{-3}$ | — | — | $10^{-3}$ | — | — | — | $10^{-3}$ |
| Dye support (1) | (*) | (*) | (*) | (*) | (*) | (*) | (*) | (*) | (*) | (*) | (*) |
| Demineralized water qs | 100 g | 100 g | 100 g | 100 g | 100 g | 100 g | 100 g | 100 g | 100 g | 100 g | 100 g |

— the amounts of base and of coupler are expressed in moles
(*) Dye support (1) pH 9.5

| | |
|---|---|
| 96° ethyl alcohol | 20.8 g |
| Sodium metabisulphite as an aqueous 35% solution | 0.23 g A.M. |
| Pentasodium salt of diethylenetriaminepentaacetic acid, as an aqueous 40% solution | 0.48 g A.M. |
| C$_8$–C$_{10}$ alkyl polyglucoside as an aqueous 60% solution | 3.6 g A.M. |
| Benzyl alcohol | 2.0 g |
| Polyethylene glycol containing 8 units of ethylene oxide | 3.0 g |
| NH$_4$Cl | 4.32 g |
| Aqueous ammonia containing 20% NH$_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. After an action time of 30 minutes, the locks were rinsed, washed with a standard shampoo, rinsed again and then dried.

The dyeing results below were obtained.

Examples 12 to 29

Dyeing in Acidic Medium

The dye compositions below were prepared:

| | Examples | | | | | | | | | | | | | | | | | |
|---|---|---|---|---|---|---|---|---|---|---|---|---|---|---|---|---|---|---|
| | 12 | 13 | 14 | 15 | 16 | 17 | 18 | 19 | 20 | 21 | 22 | 23 | 24 | 25 | 26 | 27 | 28 | 29 |
| 4-(3-Imidazol-1-ylpyrrolid-1-yl)phenylamine (base) | $10^{-3}$ | $10^{-3}$ | $10^{-3}$ | $10^{-3}$ | $10^{-3}$ | $10^{-3}$ | — | — | — | — | — | — | — | — | — | — | — | — |
| [1-(4-Aminophenyl)pyrrolid-3-yl]-(3-imidazol-1-ylpropyl)-amine (base) | — | — | — | — | — | — | $10^{-3}$ | $10^{-3}$ | $10^{-3}$ | $10^{-3}$ | $10^{-3}$ | $10^{-3}$ | — | — | — | — | — | — |
| 4-[1,3']Bipyrrolid-1'-ylphenylamine (base) | — | — | — | — | — | — | — | — | — | — | — | — | $10^{-3}$ | $10^{-3}$ | $10^{-3}$ | $10^{-3}$ | $10^{-3}$ | $10^{-3}$ |
| 2-(2,4-Diaminophenoxy) ethanol dihydrochloride (coupler) | $10^{-3}$ | — | — | — | — | — | $10^{-3}$ | — | — | — | — | — | $10^{-3}$ | — | — | — | — | — |
| 3-Amino-2-chloro-6-methyl-phenol hydrochloride (coupler) | — | $10^{-3}$ | — | — | — | — | — | $10^{-3}$ | — | — | — | — | — | $10^{-3}$ | — | — | — | — |
| 2-Methyl-5-aminophenol (coupler) | — | — | $10^{-3}$ | — | — | — | — | — | $10^{-3}$ | — | — | — | — | — | $10^{-3}$ | — | — | — |
| 2-Amino-3-pyridinol (coupler) | — | — | — | $10^{-3}$ | — | — | — | — | — | $10^{-3}$ | — | — | — | — | — | $10^{-3}$ | — | — |
| 3,6-Dimethyl-1H-pyrazolo[5,1-c][1,2,4]-triazole (coupler) | — | — | — | — | $10^{-3}$ | — | — | — | — | — | $10^{-3}$ | — | — | — | — | — | $10^{-3}$ | — |
| 6-Hydroxy-1H-indole (coupler) | — | — | — | — | — | $10^{-3}$ | — | — | — | — | — | $10^{-3}$ | — | — | — | — | — | $10^{-3}$ |
| Dye support (2) | (*) | (*) | (*) | (*) | (*) | (*) | (*) | (*) | (*) | (*) | (*) | (*) | (*) | (*) | (*) | (*) | (*) | (*) |
| Demineralized water qs | 100 g | 100 g | 100 g | 100 g | 100 g | 100 g | 100 g | 100 g | 100 g | 100 g | 100 g | 100 g | 100 g | 100 g | 100 g | 100 g | 100 g | 100 g |

— The amounts of base and of coupler are expressed in moles
(*) Dye support (2) pH 7

| | Examples | | | | | |
|---|---|---|---|---|---|---|
| | 1 | 2 | 3 | 4 | 5 | 6 |
| Shade observed | Violet-blue | Blue-violet | Red-violet | Violet | Violet-blue | Red-violet |

| | Examples | | | | |
|---|---|---|---|---|---|
| | 7 | 8 | 9 | 10 | 11 |
| Shade observed | Violet | Violet-blue | Blue-violet | Chromatic red-violet | Violet |

| | |
|---|---|
| 96° ethyl alcohol | 20.0 g |
| Sodium metabisuiphite as an aqueous 35% solution | 0.23 g A.M. |
| Pentasodium salt of diethylenetriaminepentaacetic acid as an aqueous 40% solution | 0.48 g A.M. |
| $C_8$–$C_{10}$ alkyl polyglucoside as an aqueous 60% solution | 3.6 g A.M. |
| Benzyl alcohol | 2.0 g |
| Polyethylene glycol containing 8 units of ethylene oxide | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. After an action time of 30 minutes, the locks were rinsed, washed with a standard shampoo, rinsed again and then dried.

The following dyeing results were obtained.

| | Examples | | | | | |
|---|---|---|---|---|---|---|
| | 12 | 13 | 14 | 15 | 16 | 17 |
| Shade observed | Violet-blue | Blue-violet | Violet | Grey-violet | Red-violet | Grey-violet |

| | Examples | | | | | |
|---|---|---|---|---|---|---|
| | 18 | 19 | 20 | 21 | 22 | 23 |
| Shade observed | Violet-blue | Blue-violet | Violet | Grey-violet | Red-violet | Grey-violet |

| | Examples | | | | | |
|---|---|---|---|---|---|---|
| | 24 | 25 | 26 | 27 | 28 | 29 |
| Shade observed | Violet-blue | Blue-violet | Violet | Grey-violet | Red-violet | Grey-violet |

What is claimed is:

1. A compound chosen from para-phenylenediamine derivatives substituted with a pyrrolidyl group, wherein said pyrrolidyl-substituted para-phenylenediamine derivatives are chosen from derivatives corresponding to formula (I), and the addition salts thereof,

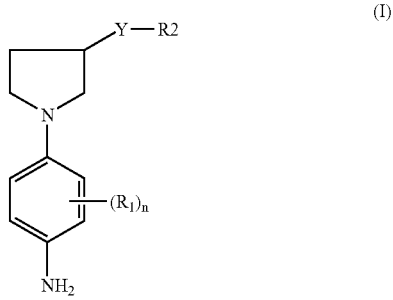

wherein:
n is an integer from 0 to 4,
provided that when n is greater than or equal to 2, then the radicals $R_1$ may be identical or different, $R_1$ is chosen from halogen atoms; saturated and unsaturated, aliphatic and alicyclic $C_1$–$C_6$ hydrocarbon-based chains, wherein at least one carbon atom of the hydrocarbon-based chain may be replaced with at least one entity chosen from oxygen, nitrogen, silicon and sulphur atoms and from SO and $SO_2$ groups,
provided that the radical $R_1$ does not comprise a peroxide bond or a diazo, nitro or nitroso radical;
and further wherein the hydrocarbon-based chain may be substituted with at least one group chosen from halogen atoms and hydroxyl, amino, mono-($C_1$–$C_4$)alkylamino, di($C_1$–$C_4$)alkylamino and tri($C_1$–$C_4$)alkylammonium radicals;

Y is chosen from a covalent bond and a linear or branched $C_1$–$C_{14}$ alkylene chain, wherein at least one carbon atom of the chain may be replaced with at least one atom chosen from oxygen, nitrogen, silicon and sulphur atoms or with a group chosen from SO and $SO_2$ groups; wherein the chain may be substituted with at least one radical chosen from hydroxyl, $C_1$–$C_6$ alkoxy, amino, $C_1$–$C_6$ alkylamino and $C_1$–$C_6$ dialkylamino radicals; and further wherein the chain may bear at least one ketone functional group, and $R_2$ is chosen from 3- to 7-membered saturated and unsaturated carbocycles and heterocycles, which may be substituted with at least one radical chosen from $C_1$–$C_6$ alkyl and $C_1$–$C_6$ hydroxyalkyl radicals.

2. The compound according to claim 1, wherein n is equal to 0 or 1.

3. The compound according to claim 1, wherein $R_1$ is chosen from halogen atoms, $C_1$–$C_4$ alkyl radicals, $C_1$–$C_4$ hydroxyalkyl radicals, $C_1$–$C_4$ aminoalkyl radicals, $C_1$–$C_4$ alkoxy radicals and $C_1$–$C_4$ hydroxyalkoxy radicals.

4. The compound according to claim 3, wherein $R_1$ is a radical chosen from methyl, hydroxymethyl, 2-hydroxyethyl, 1,2-dihydroxyethyl, methoxy, isopropyloxy and 2-hydroxyethoxy radicals.

5. The compound according to claim 1, wherein Y is a covalent bond.

6. The compound according to claim 1, wherein Y is chosen from $C_1$–$C_8$ alkylene chains, which may comprise at least one unit chosen from —O—, —NR'— and —NR'CO— wherein R' is chosen from hydrogen atoms and $C_1$–$C_4$ alkyl radicals.

7. The compound according to claim 1, wherein Y is chosen from —O—, —NR'—, —S—, —SO— and —$SO_2$—.

8. The compound according to claim 1, wherein $R_2$ is a nitrogenous heterocycle.

9. The compound according to claim 8, wherein $R_2$ is chosen from imidazole, pyrrolidine, piperazine, piperidine, triazole, diazepan and pyrazole rings.

10. The compound according to claim 8, wherein $R_2$ is linked to Y via one of the nitrogen atoms of the nitrogenous heterocycle.

11. The compound according to claim 1, wherein $R_2$ is a carbocycle chosen from $C_4$–$C_7$ cycloalkyls.

12. The compound according to claim 1, wherein $R_2$ is a phenyl radical.

13. The compound according to claim 1, chosen from
4-(3-imidazol-1-ylpyrrolid-1-yl)phenylamine,
4-(3-[1,2,4]triazol-1-ylpyrrolid-1-yl)phenylamine,
4-[1,3']bipyrrolid-1'-ylphenylamine,
4-[3-(4-methylpiperazin-1-yl)pyrrolid-1-yl]phenylamine,
4-[3-(4-methyl[1,4]diazepan-1-yl)pyrrolid-1-yl]phenylamine,
4-{3-[2-(4-methyl[1,4]d iazepan-1-yl)ethoxy]pyrrolid-1-yl}phenylamine,
4-{3-[2-(4-methylpiperazin-1-yl )ethoxy]pyrrolid-1-yl}phenylamine,
4-[3-(2-pyrrolid-1-ylethoxy)pyrrolid-1-yl]phenylamine,
4-[3-(2-piperid-1-ylethoxy)pyrrolid-1-yl]phenylamine,
[1-(4-aminophenyl)pyrrolid-3-yl]-3-imidazol-1-ylpropyl)amine,
2-methyl-[1-(4-aminophenyl)pyrrolid-3-yl](3-imidazol-1-ylpropyl)amine,
4-(3-imidazol-1-ylpyrrolid-1-yl)-2-methylphenylamine,
2-methyl-4-(3-[1, 2,4]triazol-1-ylpyrrolid-1-yl )phenylamine,
4-[1,3']bipyrrolid-1'-yl-2-methylphenylamine,
2-methyl-4-[3-(4-methylpiperazin-1-yl)pyrrolid-1-yl]phenylamine,
2-methyl-4-[3-(4-methyl-[1,4]diazepan-1-yl)pyrrolid-1-yl]phenylamine, 2-methyl-4-{3-[2-(4-methyl-[1,4]diazepan-1-yl)ethoxy] pyrrolid-1-yl}phenylamine,
2-methyl-4-{3-[2-(4-methylpiperazin-1-yl)ethoxy]pyrrolid-1-yl}phenylamine,
4-(3-pyrazol-1-ylpyrrolid-1-yl)phenylamine,
2-methyl-4-(3-pyrazol-1-ylpyrrolid-1-yl)phenylamine,
2-methyl-4-[3-(2-pyrrolid-1-ylethoxy)pyrrolid-1-yl]phenylamine and
2-methyl-4-[3-(2-piperid-1-ylethoxy)pyrrolid-1-yl]phenylamine.

14. The compound according to claim 8, chosen from
4-(3-imidazol-1-yl-pyrrolid-1-yl)phenylamine,
4-[1,3']bipyrrolid-1'-yl-phenylamine,
4-[3-(4-methylpiperazin-1-yl)pyrrolid-1-yl]phenylamine,
4-{3-[2-(4-methylpiperazin-1-yl)ethoxy]pyrrolid-1-yl}phenylamine,
4-[3-(2-pyrrolid-1-ylethoxy)pyrrolid-1-yl]phenylamine,
4-[3-(piperid-1-yl)pyrrolid-1-yl]phenylamine,
4-[3-(2-piperid-1-ylethoxy)pyrrolid-1-yl]phenylamine,
[1-(4-aminophenyl)pyrrolid-3-yl](3-imidazol-1-ylpropyl)amine,
2-methyl-[1-(4-aminophenyl)pyrrolid-3-yl](3-imidazol-1-ylpropyl)amine,
4-(3-imidazol-1-ylpyrrolid-1-yl)-2-methylphenylamine,
4-[1,3']bipyrrolid-1'-yl-2-methylphenylamine,
2-methyl-4-[3-(4-methylpiperazin-1-yl)pyrrolid-1-yl] phenylamine,
2-methyl-4-[3-(piperid-1-yl)pyrrolid-1-yl]phenylamine,
2-methyl-4-{3-[2-(4-methylpiperazin-1-yl)ethoxy]pyrrolid-1-yl}phenylamine,
4-(3-pyrazol-1-ylpyrrolid-1-yl)phenylamine,
2-methyl-4-(3-pyrazol-1-ylpyrrolid-1-yl)phenylamine,
2-methyl-4-[3-(2-pyrrolid-1-ylethoxy)pyrrolid-1-yl]phenylamine, and
2-methyl-4-[3-(2-piperid-1-ylethoxy)pyrrolid-1-yl]phenylamine.

15. A dye composition comprising at least one oxidation base chosen from pryrrolidyl-substituted para-phenylenediamine derivatives chosen from derivatives corresponding to formula (I), and the addition salts thereof

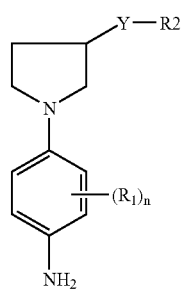

(I)

wherein
n is an integer from 0 to 4, provided that when n is greater than or equal to 2, then the radicals $R_1$ may be identical or different,
$R_1$ is chosen from halogen atoms; saturated and unsaturated, aliphatic and alicyclic $C_1$–$C_6$ hydrocarbon-based chains, wherein at least one carbon atom of the hydrocarbon-based chain may be replaced with at least one entity chosen from oxygen, nitrogen, silicon and sulphur atoms and SO and $SO_2$ groups, provided that the radical $R_1$ does not comprise a peroxide bond or a diazo, nitro or nitroso radical; and further wherein the hydrocarbon-based chain may be substituted with at least one group chosen from halogen atoms and hydroxyl, amino, mono-($C_1$–$C_4$)alkylamino, di($C_1$–$C_4$) alkylamino and tri($C_1$–$C_4$)alkylammonium radicals;

Y is chosen from a covalent bond and a linear or branched $C_1$–$C_{14}$ alkylene chain, wherein at least one carbon atom of the chain may be replaced with at least one atom chosen from oxygen, nitrogen, silicon and sulphur atoms or with a group chosen from SO and $SO_2$ groups; wherein the chain may be substituted with at least one radical chosen from hydroxyl, $C_1$–$C_6$ alkoxy, amino, $C_1$–$C_6$ alkylamino and $C_1$–$C_6$ dialkylamino radicals; and further wherein the chain may bear at least one ketone functional group, and $R_2$ is chosen from 3- to 7-membered saturated and unsaturated carbocycles and heterocycles, which may be substituted with at least one radical chosen from $C_1$–$C_6$ alkyl and $C_1$–$C_6$ hydroxyalkyl radicals.

16. The dye composition according to claim 15, further comprising at least one coupler chosen from meta-phenylenediamines, meta-aminophenols, meta-diphenols, naphthalene-based couplers, heterocyclic couplers, and the addition salts thereof.

17. The dye composition according to claim 15, comprising at least one additional oxidation base chosen from para-phenylenediamines, bis(phenyl)-alkylenediamines, para-aminophenols, ortho-aminophenols and heterocyclic bases, and the addition salts thereof,
provided that the at least one additional oxidation base does not comprise at least one compound chosen from pryrrolidyl-substituted para-phenylenediamine derivatives chosen from derivatives corresponding to formula (I), and the addition salts thereof.

18. The dye composition according to claim 17, wherein each of the oxidation bases is present in an amount ranging approximately from 0.001% to 10% by weight, relative to the total weight of the composition.

19. The dye composition according to claim 16, wherein the at least one coupler is present in an amount ranging approximately from 0.001% to 10% by weight, relative to the total weight of the dye composition.

20. The dye composition according to claim 17, further comprising at least one coupler chosen from meta-phenylenediamines, meta-aminophenols, meta-diphenols, naphthalene-based couplers and heterocyclic couplers, and the addition salts thereof.

21. The dye composition according to claim 20, wherein said at least one coupler is present in an amount ranging approximately from 0.01% to 10% by weight, relative to the total weight of the composition.

22. The dye composition according to claim 15, further comprising a cosmetically acceptable medium that is suitable for dyeing keratin fibers.

23. The dye composition according to claim 15, further comprising at least one oxidizing agent.

24. A process for the oxidation dyeing of keratin fibers, comprising applying to said keratin fibers, in the presence of an oxidizing agent, for a time that is sufficient to develop a desired coloration, an oxidation dyeing composition comprising at least one oxidation base, wherein said at least one oxidation base comprises at least one compound chosen from pryrrolidyl-group-substituted para-phenylenediamine derivatives chosen from derivatives corresponding to formula (I), and the addition salts thereof

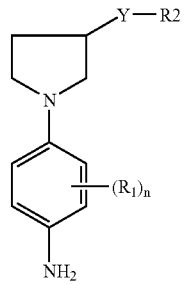

(I)

wherein
- n is an integer from 0 to 4, provided that when n is greater than or equal to 2, then the radicals $R_1$ may be identical or different,
- $R_1$ is chosen from halogen atoms; saturated and unsaturated, aliphatic and alicyclic $C_1$–$C_6$ hydrocarbon-based chains, wherein at least one carbon atom of the hydrocarbon-based chain may be replaced with at least one entity chosen from oxygen, nitrogen, silicon and sulphur atoms and SO and $SO_2$ groups, provided that the radical $R_1$ does not comprise a peroxide bond or a diazo, nitro or nitroso radical; and further wherein the hydrocarbon-based chain may be substituted with at least one group chosen from halogen atoms and hydroxyl, amino, mono-($C_1$–$C_4$)alkylamino, di($C_1$–$C_4$) alkylamino and tri($C_1$–$C_4$)alkylammonium radicals;
- Y is chosen from a covalent bond and a linear or branched $C_1$–$C_{14}$ alkylene chain, wherein at least one carbon atom of the chain may be replaced with at least one atom chosen from oxygen, nitrogen, silicon and sulphur atoms or with a group chosen from SO and $SO_2$ groups; wherein the chain may be substituted with at least one radical chosen from hydroxyl, $C_1$–$C_6$ alkoxy, amino, $C_1$–$C_6$ alkylamino and $C_1$–$C_6$ dialkylamino radicals; and further wherein the chain may bear at least one ketone functional group, and
- $R_2$ is chosen from 3- to 7-membered saturated and unsaturated carbocycles and heterocycles, which may be substituted with at least one radical chosen from $C_1$–$C_6$ alkyl and $C_1$–$C_6$ hydroxyalkyl radicals.

25. The dyeing process according to claim 24, wherein the at least one oxidizing agent is chosen from hydrogen peroxide, urea peroxide, alkali metal bromates, persalts, peracids and oxidase enzymes.

26. A multi-compartment device for the oxidation dyeing of keratin fibers, wherein a first compartment contains an oxidation dyeing composition and a second compartment contains at least one oxidizing agent, wherein said oxidation dyeing composition comprises at least one oxidation base chosen from pryrrolidyl-substituted para-phenylenediamine derivatives chosen from derivatives corresponding to formula (I), and the addition salts thereof

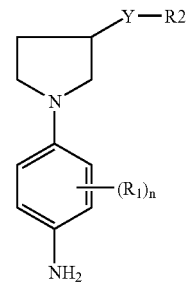

(I)

wherein
- n is an integer from 0 to 4, provided that when n is greater than or equal to 2, then the radicals $R_1$ may be identical or different,
- $R_1$ is chosen from halogen atoms; saturated and unsaturated, aliphatic and alicyclic $C_1$–$C_6$ hydrocarbon-based chains, wherein at least one carbon atom of the hydrocarbon-based chain may be replaced with at least one entity chosen from oxygen, nitrogen, silicon and sulphur atoms and SO and $SO_2$ groups, provided that the radical $R_1$ does not comprise a peroxide bond or a diazo, nitro or nitroso radical; and further wherein the hydrocarbon-based chain may be substituted with at least one group chosen from halogen atoms and hydroxyl, amino, mono-($C_1$–$C_4$)alkylamino, di($C_1$–$C_4$) alkylamino and tri($C_1$–$C_4$)alkylammonium radicals;
- Y is chosen from a covalent bond and a linear or branched $C_1$–$C_{14}$ alkylene chain, wherein at least one carbon atom of the chain may be replaced with at least one atom chosen from oxygen, nitrogen, silicon and sulphur atoms or with a group chosen from SO and $SO_2$ groups; wherein the chain may be substituted with at least one radical chosen from hydroxyl, $C_1$–$C_6$ alkoxy, amino, $C_1$–$C_6$ alkylamino and $C_1$–$C_6$ dialkylamino radicals; and further wherein the chain may bear at least one ketone functional group, and
- $R_2$ is chosen from 3- to 7-membered saturated and unsaturated carbocycles and heterocycles, which may be substituted with at least one radical chosen from $C_1$–$C_6$ alkyl and $C_1$–$C_6$ hydroxyalkyl radicals.

* * * * *